United States Patent [19]

Carpenter et al.

[11] Patent Number: 5,270,352

[45] Date of Patent: * Dec. 14, 1993

[54] SURFACE-MODIFIED MICACEOUS PARTICULATES HAVING IMPROVED DISPERSIBILITY IN AQUEOUS MEDIA

[75] Inventors: Clint W. Carpenter, Plymouth; Thomas G. Savino, Northville; Alan L. Steinmetz, Milford, all of Mich.

[73] Assignee: BASF Corporation, Southfield, Mich.

[*] Notice: The portion of the term of this patent subsequent to May 7, 2008 has been disclaimed.

[21] Appl. No.: 793,503

[22] Filed: Nov. 15, 1991

Related U.S. Application Data

[60] Division of Ser. No. 530,122, May 29, 1990, abandoned, which is a continuation-in-part of Ser. No. 376,467, Jul. 5, 1989, abandoned.

[51] Int. Cl.$^5$ .............................................. C08K 9/06
[52] U.S. Cl. ...................................... 523/213; 523/212; 428/405
[58] Field of Search ................. 523/212, 213; 428/405

[56] References Cited

U.S. PATENT DOCUMENTS

| | | | |
|---|---|---|---|
| 4,062,693 | 12/1977 | Berger | 428/404 |
| 4,184,880 | 1/1980 | Huber et al. | 106/417 |
| 4,435,220 | 3/1984 | Watanabe et al. | 106/415 |
| 4,482,389 | 11/1984 | Franz et al. | 106/418 |
| 4,509,988 | 4/1985 | Bernhard | 106/418 |
| 5,013,770 | 5/1991 | Carpenter et al. | 523/213 |

Primary Examiner—Paul R. Michl
Assistant Examiner—Edward J. Cain
Attorney, Agent, or Firm—Paul L. Marshall; Anne Gerry Sabourin

[57] ABSTRACT

Compounds useful for improving the dispersibility of micaceous particulates in aqueous-based coating compositions comprise urethanes or ureas which are the reaction products of silylalkyl or silylaryl isocyanates with alcohols, amines, polyether alcohols or amine-terminated polyethers. The compounds may also be the reaction products of silylalkyl- or silylarylamines with half-blocked diisocyanates which are themselves the reaction products of a diisocyanate with an alcohol, amine, polyether alcohol or amine-terminated polyether.

Micaceous particulates which have been surface modified by reaction with these compounds, as well as coating compositions comprising such surface-modified micaceous particulates, and coated substrates are also disclosed.

13 Claims, No Drawings

SURFACE-MODIFIED MICACEOUS PARTICULATES HAVING IMPROVED DISPERSIBILITY IN AQUEOUS MEDIA

The present application is a divisional application of application Ser. No. 07/530,122 filed May 29, 1990, pending at the time of filing the divisional application and now abandoned. Ser. No. 07/530,122 is a CIP of U.S. Ser. No. 07/376,467 filed Jul. 5, 1989, pending at the time of filing of the CIP application and now abandoned.

TECHNICAL FIELD OF THE INVENTION

This application is a continuation-in-part of U.S. Ser. No. 07/376,467 filed Jul. 5, 1989, the disclosure of which is hereby incorporated by reference.

The present invention relates to decorative coating systems primarily suited for use in the field of automotive coating. More particularly, this invention concerns compounds useful for surface modification of micaceous particulates for use in automotive coating systems based upon water-borne resins, to surface-modified micaceous particulates, to coating compositions containing such surface-modified micaceous particulates, and to substrates coated with such coating compositions.

BACKGROUND OF THE INVENTION

Multi-layer coating systems have been used to coat automotive vehicles for a number of years, but the early development of these systems necessarily employed systems based upon organic solvents ("solvent-borne" systems). As environmental concern over the use of volatile organic solvents has grown and the cost of such solvents has increased, solvent-borne coating systems have become less desirable. Recent research efforts in the coatings art have therefore focused on the development of water-borne coating systems.

The shift from organic solvents to water for dispersing and applying the resins, pigments and other components of a coating system has addressed many of the environmental and cost concerns of solvent-borne systems, but has at the same time introduced problems peculiar to water-borne coatings. One such problem relates to the use of micaceous particulates in water-borne coating systems to achieve so-called "metallic" effects in automotive coatings.

Metallic effects are generally achieved in automotive coatings by incorporating into the pigmented base coat composition of a multi-layer coating system of highly reflective, finely divided particulates. The particulates are generally aluminum flake, mica particles, or mica particles which have been encapsulated or coated with a metal oxide, typically iron oxide or titanium dioxide. Distribution of the finely divided reflective particulates throughout the cured base coat layer produces a metallic sparkle effect which is popular with the automotive consuming public.

However, mica particulates and metal oxide encapsulated or coated mica particulates do not disperse well in water-borne coating systems. This problem affects both the formulation and storage of the wet coating compositions and the appearance of the finished coating. In formulating wet coating compositions, often special processing considerations must be given to insuring the uniform incorporation of micaceous particulates to avoid aggregation of the particles. The resulting compositions are also frequently unstable, having short shelf lives. Precipitation of the micaceous particulates from the wet coating compositions results in hard, dry deposits of micaceous particulates in the bottom of containers. These deposits cannot usually be stirred back into the coating formulation, and the batch must be discarded. To counter this latter problem, it is often necessary to make up water-borne coating compositions just prior to use.

In base coat layers deposited from water-borne coating compositions containing micaceous particulates, the desired orientation of the platelet faces generally parallel to the base coat surface is frequently not optimized. The particles often orient at random angles which deviate in varying amounts from parallel to the base coat surface. When the particles have longitudinal dimensions on the order of 50 $\mu$m, the particles are longer than typical base coat layer thicknesses. Particles which are oriented at rakish angles will thus protrude through the upper surface of the base coat, contributing to an undesirable generally "fuzzy" appearance to the finished coating. Moreover, when the particles do orient generally parallel to the base coat surface, there is often a tendency of the particles to congregate near the bottom surface of the base coat layer, i.e. the surface nearest the substrate. In these cases, colored pigments in the base coat layers can hide or mask a fraction of the mica particles, diminishing to some extent the desired metallic effect of the coating.

There is thus a need in the coatings art of a means of overcoming these problems when micaceous particulates are employed in water-borne coatings systems.

SUMMARY OF THE INVENTION

The present invention provides, in one aspect a class of compounds for use in surface modification of micaceous particulates to improve the dispersibility of such particulates in water-borne coating compositions. By the term "micaceous particulates" as used throughout this specification and the appended claims is meant particulate materials comprising mica, and metal oxide coated or encapsulated micas. The class of surface modifying compounds of this invention have the general formula

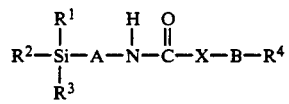

where $R^1$, $R^2$, and $R^3$ may be the same or different and are selected from alkyl of from one to ten carbon atoms, alkoxyl of from one to ten carbon atoms, alkoxyalkoxyl of from two to ten carbon atoms, alkanoyloxy of from two to ten carbon atoms, or halogen, with the proviso that $R^1$, $R^2$, and $R^3$ may not all be alkyl. The group "A" is a divalent radical selected from straight or branched alkylene of from one to twelve carbon atoms, phenylene or phenylene substituted with halogen, or alkyl or alkoxyl of from one to four carbon atoms. The group "X" is a divalent radical selected from either —O— or —NH—.

The group "B" is a direct valence bond or is a divalent group selected from the group consisting of:

a) $-(CH_2)_2-NH-CO-Y-$
b) $-(CH_2)_3-NH-CO-Y-$

-continued
c) —(CH₂)₄—NH—CO—Y—
d) —(CH₂)₅—NH—CO—Y—
e) —(CH₂)₆—NH—CO—Y—
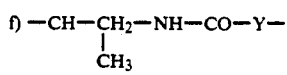
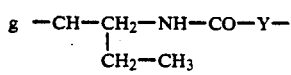
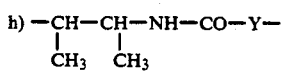
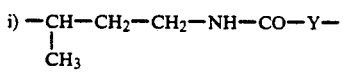
j) 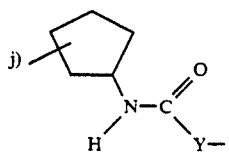
k) 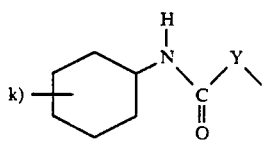
l) 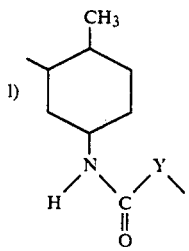
m) 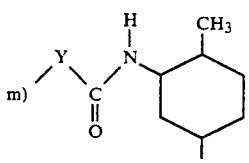
n) 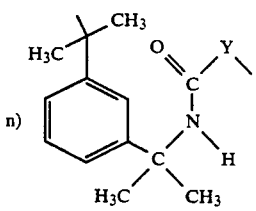
o) 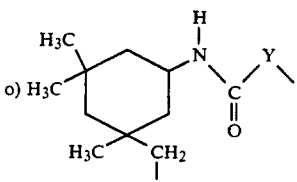
-continued
p) 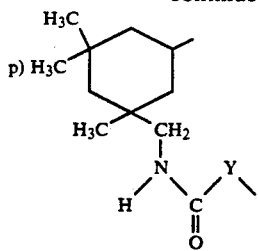
q) 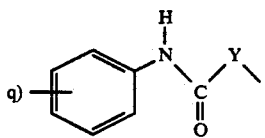
r) 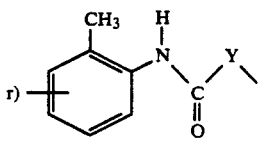
s) 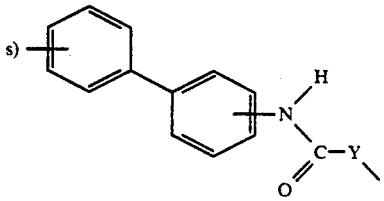
t) 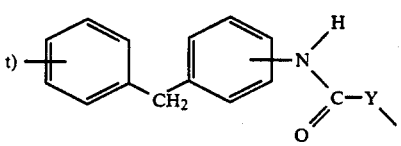
u) 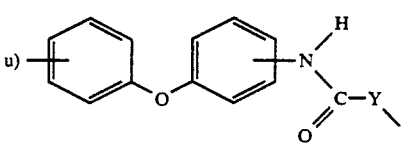
v) 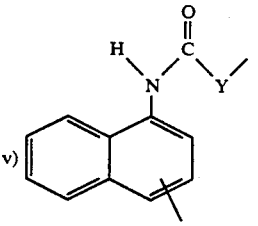
w) 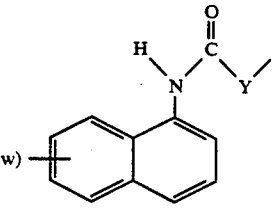
where the group Y is a divalent radical selected from —O— or —NH—.
The group R⁴ is

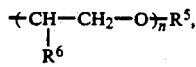

and n is an integer of from zero to 1000 or any range or subranges there between. The group $R^6$ is hydrogen or alkyl of from one to eight carbon atoms, and $R^5$ is alkyl of from one to twenty-two carbon atoms.

In all of the above formulae, it is to be understood that the carbon free-valence bond of the isocyanato group of "B" is attached to the group designated "X" and the free-valence bond of Y is attached to the group designated $R^4$.

As used throughout this specification and the appended claims, the term "alkyl" denotes a monovalent hydrocarbon radical derived by the removal of a single hydrogen atom from a branched or unbranched chain saturated hydrocarbon molecule, for example, methyl, ethyl, propyl, iso-propyl, etc. The term "alkoxyl" denotes a monovalent radical derived by removal of the hydroxyl hydrogen from a straight or branched chain alcohol, for example methoxyl, ethoxyl, etc. The term "alkoxylalkyl" denotes a monovalent radical derived by removal of a hydrogen atom from an ether, for example groups such as ethoxyethyl ($CH_3CH_2-O-CH_2-$). The term "alkoxylalkoxyl" denotes a monovalent radical derived by the removal of the hydroxyl hydrogen from a diol monoether, for example groups such as $CH_3CH_2-O-CH_2-O-$. The term "alkanoyloxy" denotes a monovalent radical derived by removal of the acidic hydrogen from a straight or branched carboxylic acid as, for example, groups such as acetyloxy ($CH_3COO-$). The term "phenylene" denotes a divalent radical derived by removal of two hydrogen atoms from benzene, and "alkylene" denotes a divalent radical derived by removal of two hydrogen atoms from a straight or branched chain saturated hydrocarbon.

In another embodiment of the present invention, there is provided a surface modified micaceous material which comprises the product derived from treatment of mica or a metal oxide encapsulated mica with a compound described above. By the term "treatment" is meant contacting the mica or metal oxide coated or encapsulated mica with the compound, with or without a solvent, with or without heating, followed by physical separation of the mica by a suitable process such as filtration and subsequent heating to complete the reaction of the surface modifying compound with reactive groups on the surface of the mica particles.

Suitable micaceous materials utilizable in this embodiment of the invention are muscovite (potassium aluminum silicate) or phlogopite (magnesium aluminum silicate) micas or mixtures thereof or either of these types of mica or their mixtures which have been surface treated with a metal oxide such as iron oxide or titanium dioxide (anatase or rutile). In addition, iron oxide coated micas which further contain absorption colorants in the coating may also be used. Materials of this type include iron oxide encapsulated micas which contain absorption colorants such as ferric ferrocyanide (C.I. 77510), and carmine (C.I. 75470).

These mica or metal oxide coated or encapsulated micas generally have particle sizes ranging in thickness of from about 0.3 μm to about 0.8 μm with the longest dimension of most platelets ranging from about 5 μm to about 90 μm. Micaceous particle platelets having their longest dimension in the range from about 5 μm to about 25 μm have a higher diffuse reflectance, producing finishes with a soft satin luster. Platelets having their longest dimension in the range of between about 10 μm to about 50 μm have high specular reflectance and produce finishes with highest luster. Those platelets having their longest dimension in the range of from about 10 μm to about 90 μm have low opacity and produce finishes with the best "sparkle" effect.

Particulate micas and metal oxide coated or encapsulated particulate micas suitable for use in producing the surface treated micas of this invention are described in "Nacreous (Pearlescent) Pigments and Interference Pigments," by L. M. Greenstein in *The Pigment Handbook, Volume 1, Properties and Economics*, Peter A. Lewis, Ed., John Wiley & Sons, New York, 1988, which is incorporated herein by reference. Micas and metal oxide encapsulated or coated micas are commercially available from a number of suppliers, including The Mearl Corporation, 41 East 42d Street, New York, N.Y. 10017 and EM Industries, 5 Skyline Drive, Hawthorne, N.Y. 10532.

In yet another embodiment of the present invention, there are provided coating compositions suitable for use as the base coat composition of a multi-layer coating system which comprise a water-borne film-forming resin, a cross-linking agent, a pigment, and a particulate micaceous material surface modified by treatment with a compound as described above. Suitable water-borne film-forming resins and resin dispersions are anionic polyurethane resins and dispersions and nonionic polyurethane resins and resin dispersions of the types described in U.S. Pat. Nos. 4,791,168 and 4,794,147, the contents of which are incorporated herein by reference. Water-borne film-forming resins and resin dispersions based upon acrylic monomers including acrylic acid, methacrylic acid, and alkyl and hydroxyalkyl esters of acrylic and methacrylic acid of the types described in U.S. Pat. Nos. 4,403,085 and 4,518,724 may also be employed in preparing coating compositions of the present invention.

In another embodiment of the present invention there are provided substrates coated with a cured film formed from coating compositions comprising a particulate micaceous material surface modified by treatment with a compound as described above. Suitable substrates include metals and plastics.

DETAILED DESCRIPTION

It has been found that micaceous particulates having improved dispersibility in water-borne coating compositions and better distribution and particle orientation in cured films desposited from such compositions can be produced by surface modification of the micaceous materials with a compound in accordance with the present invention. The compounds are low molecular weight monomers or oligomers having at one end a reactive silyl functionality which is capable of hydrolyzing in acidic aqueous media to react with and bond to oxygen functionalities on the surface of mica or metal oxide encapsulated mica particulates.

In one sub-generic aspect of this invention, the remainder of the compound comprises an alkyl or aryl urethane or urea. The urethane or urea portion of the molecule may derive from a $C_{1-22}$ alcohol or amine, or from a polyether alcohol or polyether amine containing one to one thousand alkylene oxide units. Preferred compounds of this type are those containing from about 30 to about 50 alkylene oxide units.

The compounds of this particular type are prepared, as discussed in detail below, by reaction of a alkoxylsilyl isocyanate with the desired alcohol or amine to form the product urethane or urea. Preferably, the alkoxylsilyl isocyanate is reacted with a polyether alcohol or amine-terminated polyether to provide the product urethane or urea. The incorporation into the compound of a polyether chain enhances the water-miscibility of the material, in turn enhancing the water dispersibility of the micaceous materials which are subsequently treated with the compounds.

In an alternative sub-generic aspect of the invention, the compounds of this invention have at one end a hydrolyzable silyl functionality, with the remainer of the molecule comprising a diisocyanate moiety linked to an alcohol, amine, polyether alcohol, or amine-terminated polyether. The compounds of this particular type are prepared, as discussed in detail below, by reaction of a silylamine with a half-blocked diisocyanate which has been previously reacted with an alcohol, an amine, a polyether alcohol or an amine-terminated polyether. Diisocyanates which may be used to prepare compounds of this type include ethylene diisocyanate, 1,3-propylene diisocyanate, 1,4-butylene diisocyanate, 1,5-pentylene diisocyanate, 1,6-hexylene diisocyanate, 1,2-propylene diisocyanate, 1,2-butylene diisocyanate, 2,3-butylene diisocyanate, 1,3-butylene diisocyanate, the cyclopentane diisocyanates, the cyclhexane diisocyanates, 2-methyl-1,5-cyclohexane diisocyanate, 1,3-bis-(2-isocyanato-2-propyl)benzene ("TMXDI"), isophorone diisocyanate, phenylene diisocyanate, 2,4-toluene diisocyanate, 2,6-toluene diisocyanate, the biphenyl diisocyanates such as 4,4'-biphenyl diisocyanate, the diphenylmethane diisocyanates such as 4,4'-bis-(isocyanatophenyl)methane, and the naphthalene diisocyanates such as 1,4-naphthalene diisocyanate and 1,5-naphthalene diisocyanate.

In compounds of this type having a diisocyanate moiety, preferred compounds also include a poly(alkylene oxide) group of from one to one thousand alkylene oxide units, preferably about 30 to 50 alkylene oxide units.

Particular sub-classes of compounds falling within the scope of the present invention include those having the following structural formulae:

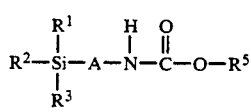

wherein A, $R^1$, $R^2$, $R^3$, and $R^5$ are as defined above;

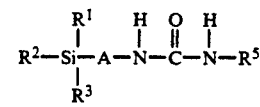

wherein A, $R^1$, $R^2$, $R^3$, and $R^5$ are as defined above;

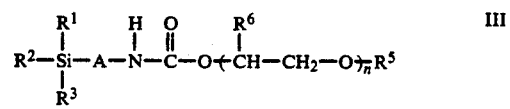

wherein A, n, $R^1$, $R^2$, $R^3$, $R^5$, and $R^6$ are as defined above;

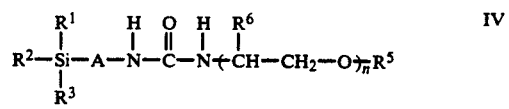

wherein A, n, $R^1$, $R^2$, $R^3$, $R^5$, and $R^6$ are as defined above;

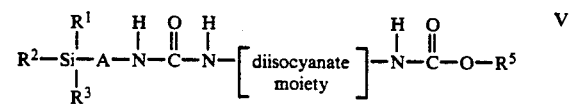

wherein A, n, $R^1$, $R^2$, $R^3$, $R^5$, and $R^6$ are as defined above, and "diisocyanate moiety" denotes a divalent radical derived from a diisocyanate compound of the group recited above by removal of the two isocyanate functionalities;

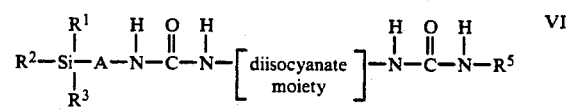

wherein A, n, $R^1$, $R^2$, $R^3$, $R^5$, $R^6$, and "diisocyanate moiety" are as defined above;

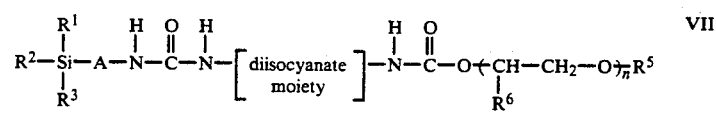

wherein A, n, $R^1$, $R^2$, $R^3$, $R^5$, $R^6$, and "diisocyanate moiety" are as defined above, and

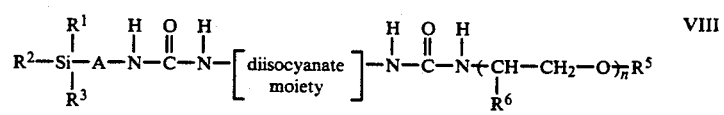

wherein A, n, $R^1$, $R^2$, $R^3$, $R^5$, $R^6$, and "diisocyanate moiety" are as defined above.

Compounds of sub-classes III, IV, VII, and VIII, above are preferred, with compounds of sub-class III being particularly preferred.

GENERAL PREPARATIVE METHODS

Preparation of Compounds of Formula I

Compounds of formula I, above, are generally prepared by reacting a silylalkyl or silylaryl isocyanate of the formula

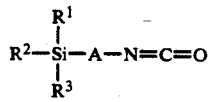

IX where A, $R^1$, $R^2$, and $R^3$ are as previously defined, with a $C_{1-22}$ alcohol. The reaction is generally carried out by mixing equimolar amounts of the reactants, optionally, with a small amount of a condensation catalyst such as dibutyl tin dilaurate, and heating the mixture for a period of up to about eight hours to effect substantially complete reaction between the isocyanate and the alcohol. The course of the reaction is followed by infrared spectroscopic analysis and the reaction is stopped at the point where the isocyanate absorption band no longer appears in the infrared spectrum of the reaction mixture. Compounds of formula IX can be generally prepared by reaction of silyl-substituted amines of formula XI (vide infra) with carbon monoxide in the presence of palladium chloride catalyst. (See, for example, Stern and Spector, *J. Org. Chem.*, 31:596 (1966). The silyl-substituted amines are commercially availble, for example from Petrarch Systems, Bartram Road, Bristol, Pa. 19007.

Compounds of the type where $R_1$, $R_2$, and $R_3$ are lower alkoxyl and A is alkylene, are available from Union Carbide Corp., 270 Park Avenue, New York, N.Y. 10017. A particularly preferred alkoxylsilylalkyl isocyanate of the type represented by formula IX above is Union Carbide Y9030.

Preparation of Compounds of Formula II

Similarly, compounds of formula II above are prepared by reacting the appropriate silylalkyl or silylaryl isocyanate of formula IX with a $C_{1-22}$ amine. The reaction is generally carried out by charging the silylalkyl or silylaryl isocyanate to the reaction vessel and heating to a temperature of between about 40° C. to about 80° C., preferably about 60° C. The amine, which may be either a monoalkylamine or a dialkylamine, is then added slowly to the reaction vessel contents. Following addition of the amine, the resulting mixture is held at a temperature of between 40° C. and 80° C. for a period of up to one hour, or until the reaction is substantially complete. The course of the reaction is followed by infrared spectroscopic analysis and the reaction is stopped at the point where the isocyanate absorption band no longer appears in the infrared spectrum of the reaction mixture.

Preparation of Compounds of Formula III

Compounds of formula III above are generally prepared by first reacting the desired $C_{1-22}$ alcohol (represented by $R^5$ in the structural formula) with ethylene oxide or the desired alkyl-substituted oxirane to produce a poly(alkylene oxide) of formula X:

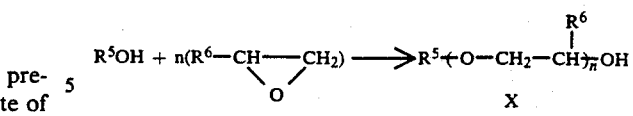

$R^6$ may be hydrogen or alkyl of from one to eight carbon atoms, with ethylene oxide and propylene oxide and mixtures thereof being preferred. In the product of this reaction, n ranges between 1 to about 1000, preferably between about 30 to about 60. The product is a polyether alcohol, which is terminated at one end by a hydroxyl group and at the other end by the $C_{1-22}$ alkoxyl group derived from the alcohol used to initiate the polymerization reaction. Preferred alcohols for initiating the reaction are lower alkanols of from one to six carbon atoms, most preferably methanol or ethanol. That is, in compounds of formula X, $R^5$ is preferably $CH_3$— or $CH_3CH_2$—. Compounds of formula X, where $R^5$ is $CH_3$— and $R^6$ is hydrogen are methoxy poly(ethylene oxide) alcohols and are generally known in the art as "MPEG's," and are commercially available in a variety of molecular weight ranges from Union Carbide Corp., 270 Park Avenue, New York, N.Y. 10017.

The polyether alcohol of formula X is next reacted with the silylalkyl or silylaryl isocyanate of formula IX above by mixing equimolar amounts of the reactants with, optionally, a small amount of a condensation catalyst such as dibutyl tin dilaurate, and heating the mixture for periods of up to about eight hours or until the reaction is substantially complete. The course of the reaction is followed by infrared spectral analysis and the reaction is stopped at the point where the isocyanate absorption band no longer appears in the infrared spectrum of the reaction mixture.

Preparation of Compounds of Formula IV

Compounds of formula IV are prepared in a manner similar to that described above for compounds of formula III. An amine-terminated poly(alkylene oxide) of formula XI is first prepared by a reaction between the desired alcohol of formula $R^5OH$ and ethylene oxide or the desired alkylene oxide as described above until the desired average molecular weight of the polymer is achieved. Then an aziridine (typically propylene aziridine) is added to the reaction mixture to terminate the growing polymer chains with an amine functionality.

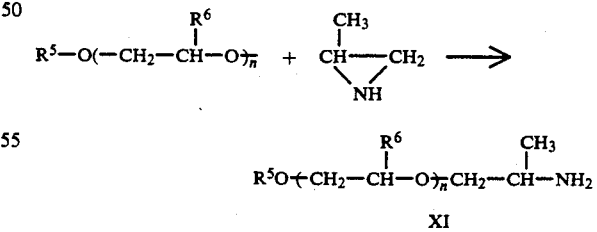

XI

The amine-terminated polyether of formula XI is then reacted with the silylalkyl or silylaryl isocyanate of formula IX above to produce the compounds of formula IV where n ranges between 1 and about 1000, preferably between about 30 and about 60. Particularly preferred compounds of formula XI are monoamine-terminated poly(ethylene oxide), poly(propylene oxide) and mixed poly(ethylene oxide) poly(propylene oxide) polyether amines sold under the tradename Jeffamine® M-600, Jeffamine® M-1000, Jeffamine® M-2000, and Jeffamine® M-2070 by Texaco Chemical Company, 4800 Fournace Place, P.O. Box 430, Bellaire, Tex. 77401. In these commercially available materials, the tradename number designates the approximate molecular weight of the polyether amine.

The polyether amine of formula XI is then reacted with the silylalkyl or silylaryl isocyanate of formula IX above to produce the compounds of formula IV. This reaction is generally carried out in an inert, aprotic organic solvent at a temperature of from about 40° C. to 60° C. for a period sufficient to bring about substantially complete reaction between the starting materials. As described above, the course of the reaction is followed by infrared spectral analysis until there is no further indication of the presence of isocyanate functionality.

Preparation of Compounds of Formula V

The compounds of formula V above are prepared by first reacting the desired diisocyanate, compound XII, with the desired $C_{1-22}$ alcohol, $R^5OH$ to produce a half-blocked isocyanate, XIII

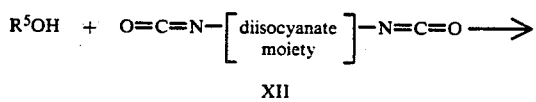

XII

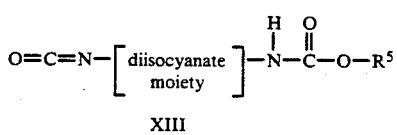

XIII

This reaction is generally carried out by first dissolving the desired diisocyanate compound in an inert, aprotic solvent such as dichloromethane and heating to a temperature of between ambient and about 60° C., preferably about 40° C. An equimolar amount of the alcohol compound is then slowly added, after which the temperature is maintained at between ambient and about 60° C. overnight, or until the reaction is substantially complete. The course of the reaction is followed by infrared spectroscopic analysis and is stopped when there is no further indication of isocyanate group functionality.

A silylalkyl- or silylarylamine of formula XIV is then added slowly to the reaction mixture, maintaining the temperature between ambient and about 60° C., preferably about 40° C. for about one hour or until infrared spectroscopic analysis indicates the absence of isocyanate groups, after which the solvent is removed by distillation.

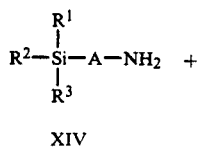

XIV

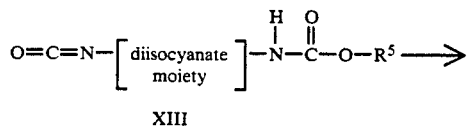

XIII

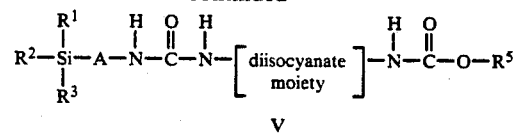

V

Preparation of Compounds of Formula VI

The compounds of formula VI above are generally prepared by first reacting the desired $C_{1-22}$ alkylamine of formula $R^5NH_2$ with the desired diisocyanate to form the half-blocked diisocyanate compound XV.

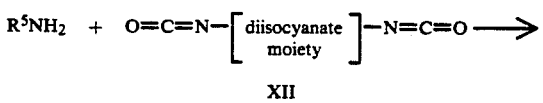

XII

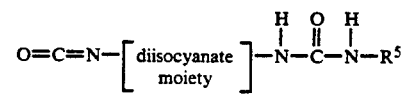

XV

This reaction is carried out in a suitable low-boiling, inert, aprotic solvent such as pentane or hexane at a temperature of about $-78°$ C. The diisocyanate compound, XII is dissolved in the solvent, the mixture is cooled, and an equimolar amount of the amine, $R^5NH_2$, is added slowly. The mixture is allowed to react for a period of about eight hours or until the reaction is substantially complete. The mixture is allowed to warm to ambient temperature, and the silylalkyl- or silylarylamine, compound XIV is added slowly. The ensuing reaction is allowed to proceed until infrared spectroscopic analysis indicates the absence of isocyanate functionality. The solvent is removed to recover the compound of formula VI.

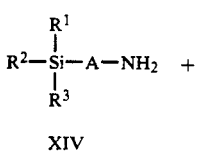

XIV

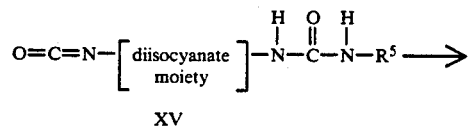

XV

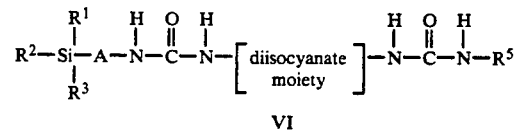

VI

Preparation of Compounds of Formula VII

The compounds of formula VII above are generally prepared by first forming a polyether alcohol of formula X above and then adding one mole of the polyether alcohol to at least one mole of the desired diisocyanate of formula XII to form a half-blocked diisocyanate. The half-blocked diisocyanate is subsequently reacted with the silylalkyl- or silylarylamine of formula XIV to form the compounds of formula VII above. These reactions are generally carried out under the conditions described above.

Preparation of Compounds of Formula VIII

The compounds of formula VIII are generally prepared by first preparing a polyether amine of formula XI as described above. The polyether amine is next reacted with the desired diisocyanate to form the half-blocked diisocyanate which is subsequently reacted with the silylalkyl- or silylaryl amine of formula XIV to form the compounds of sub-formula VIII. These reactions are generally carried out under the conditions described above.

The surface modifying compound, prepared according to one or more of the methods detailed above, is used to modify the surface of a micaceous particulate material. The surface treatment compound of formulae I through VIII above, or any mixture thereof, is dissolved in water or a wet (i.e. water-containing) alcohol such as methanol, ethanol, propanol. Water-containing alcohols are the preferred solvents for this process. The pH of the mixture is adjusted to about pH 4.5 to about pH 5.5 by the addition of an organic acid such as acetic acid. The function of the water and acid is to hydrolyze the alkoxy groups attached to the silicon atom in the surface modification compound. The amount of water present in the wet alcohol solvents ranges between a minimum amount effective to bring about such hydrolysis, typically about five percent, to an upper limit of essentially alcohol-free water. The micaceous particulate material is then added to the aqueous alcoholic solution of the surface modification compound, and the mixture slurried for ten to fifteen minutes and then filtered. The filtered material is dried and cured by heating at about 100° C. to about 150° C., preferably at about 110° C. to about 120° C. for a period of from about one hour to about twelve hours. The surface modified micaceous particulate material is then ready for incorporation into a coating formulation, or may be stored for later use.

While not adhering to any particular theory to the exclusion of others, it is believed that the water contained in the alcoholic solvent converts the reactive groups attached to the silicon atom of the surface modification compound to hydroxyl groups. For this reason, the three groups $R^1$, $R^2$, and $R^3$, attached to the silicon atom in the surface modifying compound may not all be alkyl, which are resistant to hydrolysis under these conditions. While one or two of the substituent groups may be alkyl, it is necessary that at least one of the substituent groups attached to the silicon atom be alkoxyl, alkoxylalkoxyl, alkanoyloxy, or halogen.

The hydroxyl groups which result from hydrolysis of the substituent groups on the silcon atom then react with hydroxyl groups on the surface of the micaceous particulate material to form —Si—O—M— bonds where M represents the surface metal on the micaceous particulate material (for example silicon, iron or titanium). It is believed that the surface modification which results from the treatment of the micaceous particulate material with the compounds of the present invention is the direct covalent bonding of the surface modification compound to the micaceous particles through the —Si—O—M— bonds which form. However, the exact nature of the interaction of the surface modification compounds and the micaceous particulate material is not known exactly at the time of filing of this application. Therefore, throughout this specification and the appended claims, the terms "surface modification" and "surface modified" will be used to denote the interaction and resulting composition when micaceous particulates are treated with the compounds of the present invention of formulae I–VIII above by the method just described.

Coating compositions of the present invention are formulated by mixing the surface modified micaceous particulates of the present invention, along with other components, into water dispersible base coat compositions which are sprayed or electrostatically deposited onto metal or plastic substrates such as, for example, automotive vehicle bodies. As discussed above, a water dispersible film forming resin such as a water dispersible non-ionic polyurethane resin of the type disclosed in U.S. Pat. No. 4,794,147, a water dispersible anionic polyurethane resin of the type disclosed in U.S. Pat. No. 4,791,168, or a water dispersible acrylic resin of the type disclosed in U.S. Pat. Nos. 4,403,085 and 4,518,724 is mixed with an aminoplast resin, polyisocyanate, or other suitable cross-linking agent, a suitable grind resin, pigments, one or more rheology control agents if desired, water, and a small amount of organic solvent if needed. Other agents may be included such as various fillers, surfactants, plasticizers, stabilizers, wetting agents, dispersing agents, defoamers, adhesion promoters, and catalysts in minor amounts.

The basecoat compositions containing the surface modified micaceous particulates of the present invention are applied to a metal or plastic substrate in one or more coats using, for example, an air atomizer (Binks Model 60 spray gun, available from the Binks manufacturing Corporation, Franklin Park, Ill.), or by using other convention spray methods known in the art.

After being deposited, the basecoat compositions may be flash dried at a temperature sufficient to remove a portion of the solvent, but below that sufficient to cure the applied coating, typically temperatures within the range of from room temperature to about 145° F. (63° C.). After the first basecoat is deposited, a second basecoat and subsequent layer of basecoat, if needed or desired, can be deposited over the first either with or without flash drying. A clear, transparent top coat layer is then subsequently applied over the last base coat layer. Any known unpigmented or transparently pigmented coating agent is, in principle, suitable for use as the top coat material.

After the clear coat is applied over the base coat layer(s), the multi-layer coating is then baked to cross-link and cure the polymeric materials and to drive the small amount of residual water and/or solvent from the coating layer(s). This baking step generally involves the heating of the coated substrate for periods of from about 10 to about 60 minutes and temperatures ranging between about 150° F. (66° C.) and 300° F. (149° C.). The baking step cures the multi-layer coating to a hard, durable film.

The following representative Examples are provided to enable those skilled in the art to practice this invention. However, these Examples are merely illustrative and are not to be read as limiting the scope of the invention as defined by the appended claims.

EXAMPLE 1

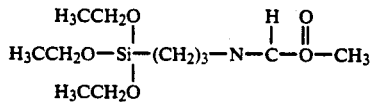

3-(Triethoxysilyl)propyl isocyanate (95.1 g, 0.38 mol) was charged to a reaction vessel fitted with a stirrer and condensor, together with a small amount of dibutyl tin dilaurate. The mixture was heated to about 118° C. and methanol (12.3 g, 0.38 mol) was slowly added to the reaction vessel contents. The temperature dropped to about 75° C. and was maintained at this level during the addition and for a period of about two hours thereafter. At the end of this time the reaction mixture was cooled and the product collected for use.

EXAMPLE 2

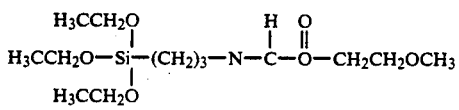

3-(Triethoxysilyl)propyl isocyanate (32.1 g 0.13 mol) was charged to a eeaction vessel fitted with a stirrer and condensor, together with a small amount of dibutyl tin dilaurate. The mixture was heated to about 105° C. and the monomethyl ether of ethylene glycol (9.9 g, 0.13 mol) was slowly added to the reaction vessel contents. The temperature was maintained at about 105°-110° C. during the addition and for a period of about two hours after addition was complete. At the end of this time the reaction mixture was cooled and the product collected for use.

EXAMPLE 3

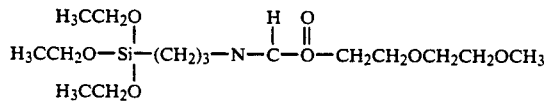

3-(Triethoxysilyl)propyl isocyanate (57.8 g, 0.23 mol) was charged to a reaction vessel fitted with a stirrer and condensor, together with a small amount of dibutyl tin dilaurate. The mixture was heated to about 107° C. and [(2-methoxy)ethoxy]ethanol ("methyl Carbitol," 28.1 g, 0.23 mol) was slowly added to the reaction vessel contents. The temperature was maintained at about 105°-110° C. during the addition and for a period of about two hours after addition was complete. At the end of this time the reaction mixture was cooled and the product collected for use.

EXAMPLE 4

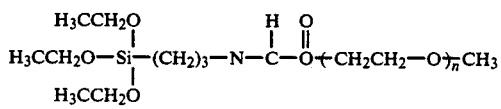

(Nominal value of n is 8)

3-(Triethoxysilyl)propyl isocyanate (84.7 g (0.34 mol) was charged to a reaction vessel fitted with a stirrer and condensor, together with a small amount of dibutyl tin dilaurate. The mixture was heated to about 85° C. and methoxypolyethylene glycol (119.2 g, 0.34 mol, available as Carbowax MPEG 350 from Union Carbide Corp., 270 Avenue, New York, N.Y. 10017) was slowly added to the reaction vessel contents. This material has an average molecular weight of about 350 Daltons. The temperature was raised to about 120° C. and maintained at this level during the addition of the MPEG and for a period of about two hours after addition was complete. At the end of this time the reaction mixture was cooled and the product collected for use.

EXAMPLE 5

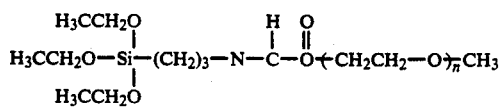

(Nominal value of n is 12)

This material was prepared using the procedure of Example 2 with 69.7 g (0.28 mol) of 3-(triethoxysilyl)-propyl isocyanate, but substituting 155 g (0.28 mol) of Carbowax ® MPEG 550 (average molecular weight 550 Daltons, available from Union Carbide Corp., 270 Avenue, New York, N.Y. 10017).

EXAMPLE 6

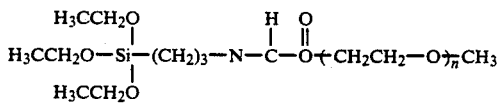

(Nominal value of n is 45)

This material was prepared using the procedure of Example 2 with 44.6 g (0.18 mol) of 3-(triethoxysilyl)-propyl isocyanate, but substituting 360 g (0.18 mol) of Carbowax ® MPEG 2000 (average molecular weight 2000 Daltons, available from Union Carbide Corp., 270 Avenue, New York, N.Y. 10017).

EXAMPLE 7

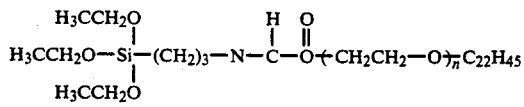

(Nominal value of n is 45)

This material was prepared using the procedure of Example 2 with 18.7 g (0.0.08 mol) of 3-(triethoxysilyl)-propyl isocyanate, but substituting 175.0 g (0.0.08 mol) of a material having the nominal formula HO—(—CH$_2$CH$_2$—O—)$_n$—C$_{22}$H$_{45}$ (where n is nominally equal to 45).

EXAMPLE 8

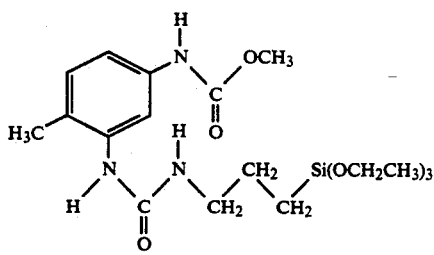

2,4-Toluene diisocyanate (49.7 g, 0.29 mol), and 9.2 g (0.29 mol) of methanol were dissolved in 200 ml of dichloromethane under nitrogen. The mixture was heated to about 40° C. and 63.1 g (0.29 mol) of 3-(triethoxysilyl)propylamine was added dropwise to the mixture. When addition was complete, the mixture was heated at about 40° C. for an additional one-half hour. At the end of this time the solvent was evaporated from the mixture and the product recovered.

EXAMPLE 9

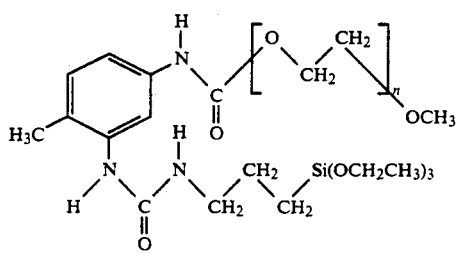

n = 1

2,4-Toluene diisocyanate (42.9 g, 0.25 mol) was dissolved in 135.7 g of dichloromethane and placed in a reaction vessel fitted with a stirrer and condensor. The flask contents were gently heated to a temperature of about 40° C. and 18.7 g (0.25 mol) of the monomethyl ether of ethylene glycol was slowly added. The mixture was maintained at about 40° C. throughout the addition and for a period of about one hour thereafter. After this time, 44.2 g (0.25 mol) of 3-(triethoxysilyl)propylamine was added dropwise to the mixture. When addition was complete, the mixture was heated at about 40° C. for an additional one-half hour. At the end of this time the solvent was evaporated from the mixture and the residue heated to 96° C. for a period of about one half hour. The flask contents were cooled to room temperature and the product recovered.

EXAMPLE 10

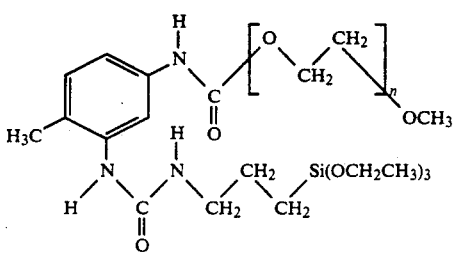

(Nominal value of n is 9)

2,4-Toluene diisocyanate (34.7 q, 0.20 mol) was dissolved in 100.3 g of diohloromethane and placed in a reaction vessel fitted with a stirrer and condensor. The flask contents were gently heated to a temperature of about 40° C. and 109.6 g (0.20 mol) of Carbowax MPEG 550 (available from Union Carbide Corp., 270 Park Avenue, New York, N.Y. 10017) was slowly added. The mixture was maintained at about 40° C. throughout the addition and for a period of about one hour thereafter. After this time, 35.7 g (0.2 mol) of 3-(triethoxysilyl)propylamine was added dropwise to the mixture. When addition was complete, the mixture was heated at about 40° C. for an additional one-half hour. At the end of this time the solvent was evaporated from the mixture and the residue heated to 80° C. for a period of about one half hour. The flask contents were cooled to room temperature and the product recovered.

EXAMPLE 11

Surface Treatment of Mica

The surface treatment compound of Example 8 (87.9 g) was dissolved in 809 g of 10% aqueous ethanol and the pH of the resulting mixture was adjusted to pH 5.2 by the addition of acetic acid. Iron oxide encapsulated mica (87.9 g, available as Afflair ® 504 Red WR, EM Industries, 5 Skyline Drive, Hawthorne, N.Y. 10532) was added to the solution and the resulting mixture was slurried for twenty minutes. After this time the solid was collected by filtration and heated at a temperature of about 110° C. for a period of twelve hours.

EXAMPLE 12

Surface Treatment of Mica

Using the same procedure as described above in Example 4, 31.7 g of the surface treatment compound of Example 3 were dissolved in 635 g of 10% aqueous ethanol and the pH of the resulting solution adjusted to pH 5.2. Iron oxide/titanium dioxide encapsulated mica (Afflair ® 504 Red WR, EM Industries, 5 Skyline Drive, Hawthorne, N.Y. 10532) was treated with this mixture as described above, collected by filtration, and dried at 110° C. for a period of sixteen hours.

EXAMPLE 13

Coating Composition

A coating composition was prepared which contained iron oxide encapsulated mica prepared in accordance with Example 11 above.

Black Tint Pigment

A black tint formulation was prepared by mixing 25.42 parts by weight of an anionic polyurethane resin, 15.35 parts by weight Cymel ® 327 methylated melamineformaldehyde resin, 0.08 parts by weight dimethylethanolamine, and 6.29 parts by weight Monarch 900 carbon black (Cabot Corporation, 125 High Street, Boston, Mass. 02110). To this mixture were then added 45.26 parts by weight anionic polyurethane resin and 7.6 parts by weight deionized water.

The anionic polyurethane resin was prepared according to the teachings of U.S. Pat. No. 4,791,168, the contents of which are incorporated herein by reference.

Red Pigment Paste #1

A red pigment paste was prepared by mixing 21 parts by weight anionic polyurethane resin, 5.91 parts by weight Cymel® 327 methylated melamine-formaldehyde resin, and 7.68 parts by weight C.I. Pigment Red 179. After stirring this mixture for thirty minutes, 54.89 parts by weight anionic polyurethane resin and 8.52 parts by weight deionized water were added with mixing. The anionic polyurethane resin was prepared in accordance with the teachings of U.S. Pat. No. 4,791,168.

Red Pigment Paste #2

A red pigment paste was prepared by mixing 24.02 parts by weight anionic polyurethane resin, 12.34 parts by weight Cymel® 327 methylated melamine-formaldehyde resin, 3.61 parts by weight high acid value acrylic grind resin, and 21.65 parts by weight red transparent iron oxide pigment. After stirring this mixture for thirty minutes, 30.91 parts by weight anionic polyurethane resin and 7.47 parts by weight deionized water were added with mixing. The anionic polyurethane resin was prepared in accordance with the teachings of U.S. Pat. No. 4,791,168.

Red Pigment Paste #3

A red pigment paste was prepared by mixing 24.14 parts by weight anionic polyurethane resin, 6.57 parts by weight Cymel® 327 methylated melamine-formaldehyde resin, and 1.72 parts by weight high acid value acrylic grind resin for ten minutes. After this time, 7.57 parts by weight of C.I. Pigment Red 202 were added with stirring. The resulting mixture was stirred for thirty minutes, after which time 60 parts by weight anionic polyurethane resin were added and the resulting mixture stirred for one hour. The anionic polyurethane resin was prepared in accordance with the teachings of U.S. Pat. No. 4,791,168.

Mica Pigment Dispersion

Surface modified iron oxide encapsulate mica particles (23.21 parts by weight), prepared in accordance with Example 12 above, was slurried into 52.21 parts by weight of a branched polyester resin. The resin solution was prepared in accordance with U.S. Pat. No. 4,791,168.

The resin dispersion was stirred vigorously enough to form a vortex and the surface-modified mica was slowly added into the vortex. When the addition was complete, 15.11 parts by weight of a 5% aqueous solution of dimethylethanolamine were added. (All parts by weight are based on 100 parts by weight of the total mica dispersion, the balance comprising ethylene glycol monobutyl ether.)

| Coating Composition | |
|---|---|
| Ingredient | Parts by Weight |
| 1. 2% Dispersion of Laponite RD in water | 28.58 |
| 2. Cymel® 327 Methylated melamine formaldehyde resin | 2.02 |
| 3. Ethylene glycol monobutyl ether | 0.50 |
| 4. Non-ionic polyurethane resin dispersion | 25.38 |
| 5. Black tint | 2.00 |
| 6. Red Pigment Paste #1 | 12.90 |
| 7. Red Pigment paste #2 | 7.60 |
| 8. Red pigment paste #3 | 5.35 |
| 9. Treated mica | 3.68 |
| 10. Ethylene glycol monobutyl ether | 4.49 |
| 11. Branched polyester resin | 5.25 |
| 12. 5% Aqueous dimethylethanolamine | 2.25 |
| | 100.00 |

Components 2 and 3 were premixed, and then added to component 1 with rapid stirring. To this mixture were then added, successively with rapid stirring, components 4–8. Components 9–12 were premixed and then added to the mixture with stirring. After mixing of all components, stirring was continued for about one hour, after which the coating composition was placed in a container and capped for later use.

EXAMPLE 14

Coating Composition (Control)

A red coating composition was prepared having the same composition as described above in Example 13 with the exception that the iron oxide encapsulated mica used had not been surface modified by treatment with a compound of the present invention.

The enhanced dispersibility in water-borne coating systems of surface modified micaceous particulates of this invention was noted by several observations. First, it was observed that when the surface modified micaceous materials of the present invention were stirred into an aqueous-based resin vehicle, the material mixed in with the resin solution almost upon contact. In the case of prior art micaceous particulates which had not been surface treated in accordance with this invention, the material tended to remain on the surface of the resin vehicle for periods up to about three minutes while only gradually mixing in with the vehicle.

Second, the paint formulation made in accordance with Example 14 above which contained untreated micaceous material was subject to settling after only twenty-four hours. That is, in this material, a layer of hard, dry micaceous material was observed on the bottom of the container of coating composition after twenty-four hours. This layer comprised the larger particles of micaceous particulates which had settled to the bottom of the container and could not be remixed into the coating composition. On the other hand, the coating composition made in accordance with Example 13 above, containing the surface modified micaceous particulate material, exhibited only slight settling upon standing for a period of about six days. In this sample, after six days standing, there was some settling of larger particles of micaceous material, but stirring restored a uniform composition.

Third, in cured base coat layers containing surface modified micaceous particulates in accordance with this invention, there was evidence of more uniform distribution of the particulates throughout the basecoat layer. Microscopic examination of the cross-section of such layers showed that the surface modified micaceous particles were more randomly distributed vertically through the base coat layers. In base coat layers prepared from coating compositions containing micaceous particles lacking the surface modification, there was observed a greater congregation of the particles toward the lower surface of the base coat layer.

Fourth, microscopic examination of base coat layers prepared from coating compositions of the present invention revealed that the surface modified micaceous particles were oriented generally parallel to the surface of the base coat layer. In the case of base coat layers desposited from compoisitions containing micaceous particulates which lacked surface modification, there was a greater tendency of the particles to orient at angles deviating from parallel to the base coat layer surface. Parallel orientation of the micaceous particles is desirable to optimize the aesthetic "metallic" effect of the cured base coat layer.

The invention has been described in detail with particular reference to preferred embodiments thereof, but it will be understood that variations and modifications can be affected within the spirit and scope of the invention as defined by the claims appended hereto.

We claim:

1. A coating composition comprising
    a) a water-borne film-forming resin;
    b) a cross-linking agent;
    c) a pigment;
    d) a particulate micaceous material surface modified by treatment with a compound having the formula

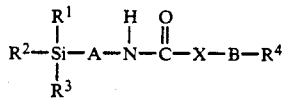

wherein
$R^1$, $R^2$, and $R^3$ may be the same or different and are selected from
  alkyl of from one to ten carbon atoms,
  alkoxyl of from two to ten carbon atoms,
  alkoxylalkoxyl of from two to ten carbon atoms,
  alkanoyloxy of from two to ten carbon atoms, or halogen,
  with the proviso that $R^1$, $R^2$, and $R^3$ may not all be alkyl;
A is a divalent radical selected from
  straight or branched alkylene of from one to twelve carbon atoms,
  phenylene, or
  phenylene substituted with
    halogen,
    alkyl of from one to four carbon atoms, or
    alkoxyl of from one to four carbon atoms;
X is a divalent radical selected from —O— or —NH—;
B is a direct valence bond or is a divalent group selected from the group consisting of a) —(CH$_2$)$_2$—NH—CO—Y—
b) —(CH$_2$)$_3$—NH—CO—Y—
c) —(CH$_2$)$_4$—NH—CO—Y—
d) —(CH$_2$)$_5$—NH—CO—Y—
e) —(CH$_2$)$_6$—NH—CO—Y— f) 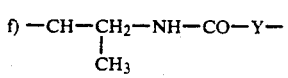

g) 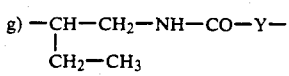

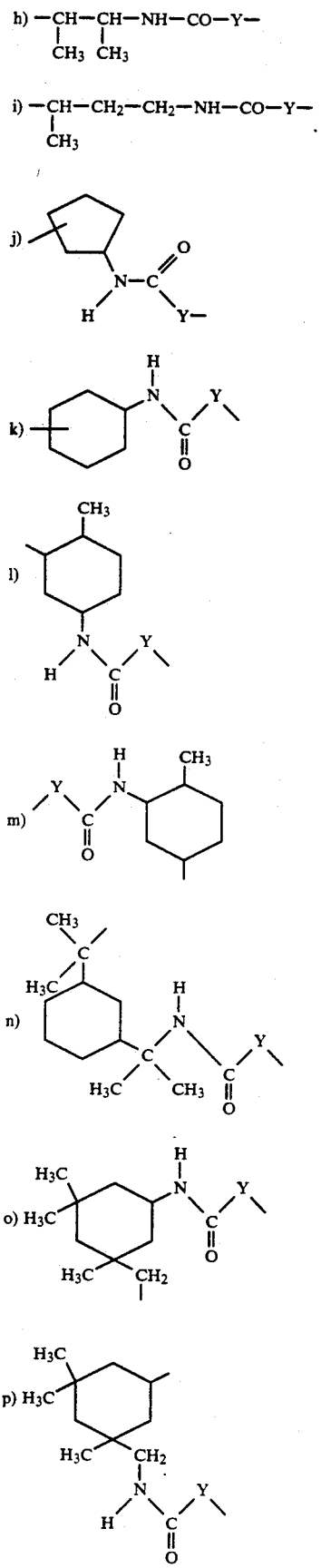

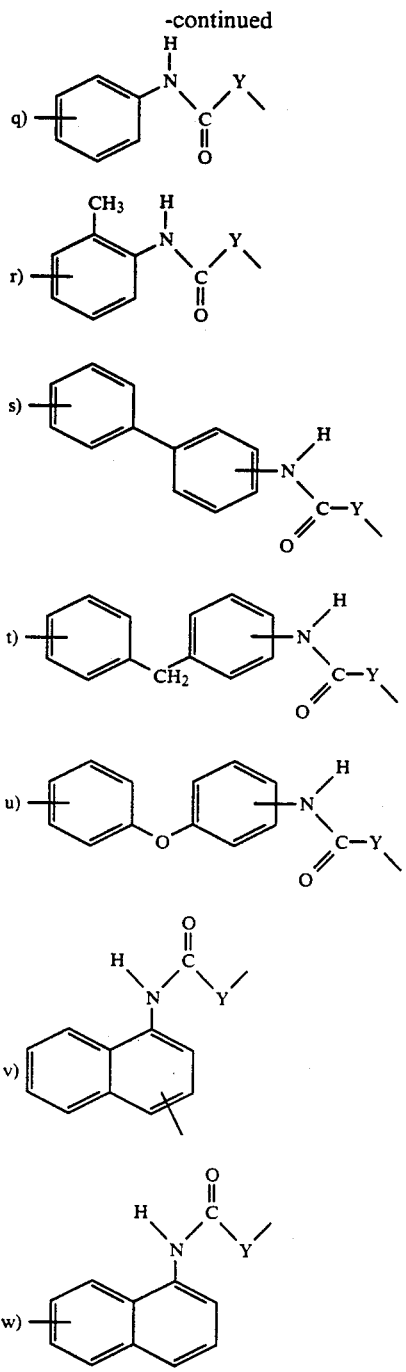

wherein Y is a divalent radical selected from —O— and —NH—;

R⁴ is

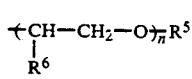

wherein n is an integer of from zero to one hundred

R⁶ is hydrogen or alkyl of from one to eight carbon atoms;

R⁵ is alkyl of from one to twenty-two carbon atoms.

2. A coating composition as defined by claim 1 wherein said particulate micaceous material comprises mica.

3. A coating composition as defined by claim 1 wherein said particulate micaceous material comprises metal oxide encapsulated mica.

4. A coating composition as defined by claim 1 wherein said metal oxide is selected from the group consisting of iron oxide and titanium dioxide.

5. A substrate coated by at least one layer of cured coating deposited from a coating composition as defined by claim 1.

6. A coating composition according to claim 1 wherein said surface-modification compound has the formula

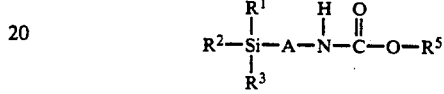

7. A coating composition according to claim 1 wherein said surface-modification compound has the formula

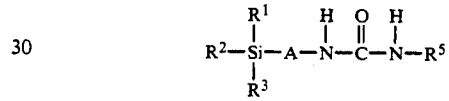

8. A coating composition according to claim 1 wherein said surface-modification compound has the formula

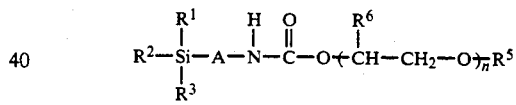

9. A coating composition according to claim 1 wherein said surface-modification compound has the formula

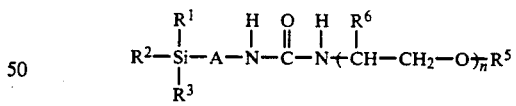

10. A coating composition according to claim 1 wherein said surface-modification compound has the formula

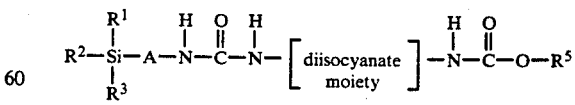

wherein diisocyanate moiety designates a divalent residue derived from a diisocyanate by removal of the two isocyanate functional groups.

11. A coating composition according to claim 1 wherein said surface-modification compound has the formula

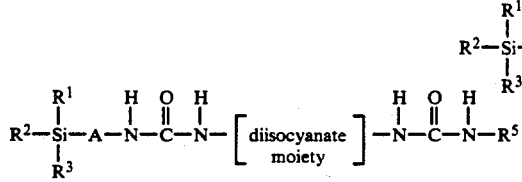

wherein diisocyanate moiety designates a divalent radical derived from a diisocyanate by removal of the two isocyanate functional groups.

12. A coating composition according to claim 1 wherein said surface-modification compound has the formula

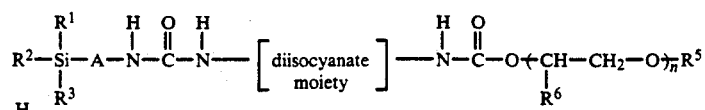

wherein diisocyanate moiety designates a divalent radical derived from a diisocyanate by removal of the two isocyanate functional groups.

13. A coating composition according to claim 1 wherein said surface-modification compound has the formula

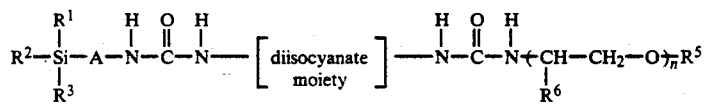

wherein diisocyanate moiety designates a divalent radical derived from a diisocyanate by removal of the two isocyanate functional groups.

* * * * *